United States Patent [19]

Chiusoli et al.

[11] Patent Number: 4,465,634

[45] Date of Patent: Aug. 14, 1984

[54] PROCESS FOR PREPARING DIENOIC ACIDS

[75] Inventors: Gian P. Chiusoli; Luciano Pallini; Giuseppe Salerno, all of Parma, Italy

[73] Assignee: Istituto Donegani S.p.A., Novara, Italy

[21] Appl. No.: 333,934

[22] Filed: Dec. 23, 1981

[30] Foreign Application Priority Data

Dec. 23, 1980 [IT] Italy .............................. 26943 A/80

[51] Int. Cl.$^3$ ........................... C11C 1/00; C09F 5/08
[52] U.S. Cl. ..................................... 260/413; 260/410
[58] Field of Search ........ 260/413 K, 413 R, 413 HC, 260/410 R

[56] References Cited

U.S. PATENT DOCUMENTS

| | | | |
|---|---|---|---|
| 2,823,216 | 2/1958 | Moote et al. | 260/413 HC |
| 3,032,583 | 5/1962 | Chiusoli et al. | 260/413 K X |
| 3,075,010 | 1/1963 | Schmerling et al. | 260/413 HC X |
| 3,493,590 | 2/1970 | Chabardes | 260/413 HC X |
| 3,644,497 | 2/1972 | Mesich | 260/410 R X |
| 4,093,815 | 6/1978 | Stapp | 260/410 R X |
| 4,123,465 | 10/1978 | Valentine | 260/413 K X |
| 4,293,499 | 10/1981 | Hughes | 260/410 R X |
| 4,309,357 | 1/1982 | Chiusoli et al. | 260/413 K |

Primary Examiner—Helen M. S. Sneed

[57] ABSTRACT

This invention relates to a process for preparing dienoic acids.

In particular, the present invention relates to a catalytic process for preparing octadienoic acids from 3-butenoic acids and butadiene.

More particularly the present invention is directed to the preparation of octadienoic acids haing the two double bonds in position 3,6 and 2,6 in respect of the carboxylic carbon, starting from 3-butenoic acids and butadiene in the presence of complex catalysts of Rhodium or of Nickel.

15 Claims, No Drawings

PROCESS FOR PREPARING DIENOIC ACIDS

BACKGROUND OF INVENTION

The products obtained are suited in themselves to interesting industrial applications as intermediates for organic syntheses, especially as regards the so-called "fine chemicals".

For example, it is possible to obtain, by simple conventional hydrogenation of the double bonds, known acids having wide applicative fields as plasticizers, solvents, additives etc., such as the octanoic acid by hydrogenation of the 3,6- and 2,6-octadienoic acid, suited for plasticizers, fluids for hydraulic brakes, etc.

Furthermore, by utilizing the reactivity of the two double bonds existing in the molecule it is possible to prepare polymers etc.

As far as applicants know, the specific reaction utilized for the process according to this invention for obtaining dienoic acids is not described in the prior art.

According to the art, by means of reactions not pertaining, however, to the one of the present invention, dienoic acids can be actually obtained, through alternative processes based on the Wittig synthesis, starting from aldehydes which are caused to react with organic phosphorous compounds.

Nevertheless, techniques of this type require the preliminary preparation of suitable aldehydes, which are sometimes difficult to be obtained or found, and the stoichiometric use of phosphorous intermediates, which are objectable as regards the compatibility of the effluents with the present environmental requirements, etc. and relevant economic burdens, which render such techniques substantially not practical from an industrial viewpoint.

Finally there are known catalytic processes for the preparation of dienoic acids by reacting unsaturated halides (vinyl, allyl halides) with acetylene and carbon monoxide in hydroxylated solvents in the presence of nickel carbonyl or precursors thereof. These methods are, from an industrial viewpoint, of minor interest for the use of nickel carbonyl derivatives and of carbon monoxide, which are not suitable for industrial applications owing to the high toxicity of the envisaged conditions.

Co-dimerization reactions of alpha-olefins (ethylene) with conjugated dienes (butadiene) in the presence of phosphinic or phosphitic complex catalysts of nickel have been described. Similarly, addition or dimerization reactions of olefins in the presence of rhodium trichloride as a catalyst have been described too; in this way 1,4-diolefins were obtained, for example 1,4-hexadiene from ethylene and butadiene, or dimethyl ester of 2-hexendioic acid from methylacrylate etc.

Nevertheless, such techniques have not proved effective for purposes of obtaining linear products, as experimentally demonstrated in literature, when applied to the co-dimerization reaction of butadiene with alkylsmonosubstituted ethylenes, since such latter ethylenes are attacked on the inner carbon atom of the double bond.

According to the present invention, conversely, in which butadiene and a 3-butenoic acid, also definable as an ethylene monosubstituted by acetic groups, are co-dimerized, the linkage product of butadiene to the outer carbon atom of the acid double bond predominantly forms; prevailingly linear products are obtained.

OBJECTS OF THE INVENTION

It is an object of the present invention to provide a simple and economic process for preparing octadienoic acids, which may be free from the drawbacks cited for the prior art. This and still other objects, will be clearly apparent to those skilled in the art from the following description:

GENERAL DESCRIPTION OF THE INVENTION

According to the present invention, a process for preparing octadienoic acids is provided, such process being characterized in that butadiene is reacted with a 3-butenoic acid of formula (I):

$$R\ R_1C=CR_2CR_3HCOOH \qquad (I)$$

wherein the symbols: R; $R_1$; $R_2$; $R_3$, either like or unlike one another, represent hydrogen atoms or alkyl groups, containing up to 4 carbon atoms, optionally containing double bonds, in an inert atmosphere and in the presence of a catalyst selected from the phosphinic complexes of Rhodium (III, IV) and the phosphitic complexes of Nickel (V and VI), better defined in the following, at a temperature ranging from 60° to 140° C., approximately.

In this way it is possible to obtain the 3,6- and 2,6-octadienoic acids of formula (IIa, b):

$$CH_3CH=CHCH_2CR_1=CR_2CR_3HCOOH \qquad (IIa)$$

$$CH_3CH=CHCH_2CRR_1CR_2=CR_3COOH \qquad (IIb)$$

wherein the symbols have the meanings specified hereinbefore.

The octadienoic acids of formula (IIa) and (IIb) substantially represent a portion, up to about 90%, of the reaction products, along with lesser amounts, up to 10-20%, of 3,6- and 2,6-(5-methyl)-heptadienoic acids having formulae (IIa') and (IIb'):

$$CH_2=CHCH(CH_3)CR_1=CR_2CR_3HCOOH \qquad (IIa')$$
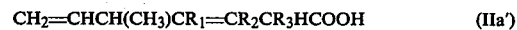

$$CH_2=CHCH(CH_3)CRR_1CR_2=CR_3COOH \qquad (IIb')$$
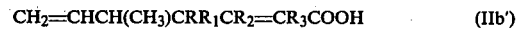

Said 3,6-octadienoic (IIa) and 3,6-(5-methyl)-heptadienoic (IIa') acids are selectively obtained by employing the phosphinic complex catalysts of Rhodium (III, IV) of the present invention.

The utilization of phosphitic complex catalysts of Nickel (V) and (VI) leads, besides to the obtainment of the acids (IIa) and (IIa') defined hereinabove, to the obtainment of more or less considerable amounts of 2,6-octadienoic isomers and of 2,6-(5-methyl)-heptadienoic isomers of formulas (IIb) and (IIb'), respectively, with the same approximate percent distribution.

From formula (IIa) it appears that symbol R=H has been eliminated, the remaining symbols having the meanings already specified.

In the simplest case, where R=$R_1$=$R_2$=$R_3$=H, the reaction may be represented by the following equation:

$$CH_2=CHCH=CH_2 + \qquad (1)$$

$$CH_2=CHCH_2-COOH \xrightarrow{\text{(compl.) Rh catalyst}}$$
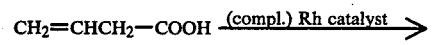

-continued
$$CH_3CH=CHCH_2CH=CHCH_2COOH +$$
(IIa)

$$CH_2=CHCH(CH_3)CH=CHCH_2COOH$$
(IIa')

wherein 3,6-octadienoic acid (IIa), about 90%, is obtained predominantly as a mixture of "3-trans-6-trans" and "3-cis-6-trans". Product (IIa'), about 10–20%, is a mixture of "trans" and of "cis".

The reaction occurs analogously also in the case in which the Nickel phosphitic catalysts (V) and (VI) are utilized, which, however, as mentioned hereinbefore, lead to the simultaneous obtainment of the 2,6-octadienoic (IIb) and 2,6-(5-methyl)-heptadienoic (IIb') acids defined hereinabove, and generally for all the other 3-butenoic acids of formula (I).

More explicitly, reaction (1) is based on the addition of butadiene to 3-butenoic acids (I), from which the hydrogen atoms in position 2 or 4 are eliminated, thus obtaining, respectively, the addition "3,6" and "2,6" - dienoic acids.

In contrast with what is substantially described or suggested by the art discussed hereinbefore, according to the present invention there is obtained a practically selective linking of butadiene to position "4" of 3-butenoic acids (I), whereby the linear derivative is prevailingly obtained. The abovesaid circumstance represents the surprising essential feature typical of the process object of the present invention.

The reaction is conducted in the absence of a real solvent, an excess of the 3-butenoic acid (I) employed being capable of acting as an organic medium. Nevertheless the reaction may be conducted in an organic solvent not containing aliphatic unsaturations and selected from those belonging to the classes, of the alcohols, such as ethyl alcohol, of the ethers, such as anisole, of the esters, such as ethyl acetate, of the hydrocarbons, such as benzene, of the nitriles, such as acetonitrile, of the carboxylic acids, such as acetic acid.

Said solvent, to facilitate the separation of the products and of the reagents (distillation), has preferably a lower boiling point than that of the 3-butenoic acid employed.

The catalyst is selected from amongst the complexes of monovalent Rhodium with phosphines and the complexes of Nickel with phosphites having the formulae:

$$Rh[P(R_4)_3]_nL_mX \qquad \text{(III)}$$

$$Rh[P(R_4)_3]_nL^+_pY^- \qquad \text{(IV)}$$

$$Ni[P(OR_5)_3]_4 \qquad \text{(V)}$$

$$Ni(COD)_{2+q} P(OR_5)_3 \qquad \text{(VI)}$$

wherein $R_4$ represents a hydrocarbyl group having up to 15 carbon atoms, optionally substituted with inert groups; "L" represents a linear or cyclic olefin having from 2 to 10 carbon atoms or a chelating olefin having from 6 to 10 carbon atoms; n is an integer ranging from 1 to 3; m is an integer from 0 to 2, such that $n+m=2$ or 3; p is an integer from 0 to 3 and such that $n+p=3$ or 4; COD represents 1,5-cyclooctadiene and q is an integer from 1 to 4; X is an anion selected from the haloid anions, preferably the hydrochloric anion, and the anions of carboxylic acids having up to 4 carbon atoms; Y is selected from amongst $BF_4^-$, $PF_6^-$; $ClO_4^-$, $B(Ph)_4^-$, wherein Ph is a phenyl; $R_5$ is an aryl or an alkyl having up to 12 carbon atoms.

Generally, low coordinating Y anions may be used.

Said complexes of Rhodium (III) and (IV) or of Nickel (V) and (VI) are known in themselves and commercially available, or they can be prepared according to conventional methods.

For example, by reduction of Rhodium salts in the presence of a ligand (phosphine) etc., or by reduction of Nickel salts in the presence of phosphites etc.

Such preparation may be also effected "in situ", starting from the original reagents.

In any case it is possible to operate also in the presence of an excess of the ligand phosphine or phosphite.

In particular, effective results have been obtained by employing, for the catalysts of Rh (III) and (IV), complexes in which $R_4$ is an aliphatic or aromatic group having up to 15 carbon atoms, optionally substituted by inert groups under reaction conditions, such as for example for $OCH_3$ group.

Operative groups are the propyl, iso-propyl, butyl, cyclo-hexyl groups among the alkyl groups, the phenyl, tolyl, anisyl, diphenyl, naphthyl groups among the aromatic groups.

Olefin L is preferably selected from ethylene, cyclooctene, norbornene; the chelating olefins from 1,5-cyclooctadiene, 1,5-hexadiene, norbornadiene and dicyclopentadiene.

As regards the catalysts based on Nickel (V) and (VI), effective results are obtainable with $R_5$ groups composed of aryl or alkyl groups having up to 12 carbon atoms, such as the isopropyl, phenyl, etc. groups.

In the catalyst of formula (VI) based on Nickel, COD (1,5-cyclooctadiene) may be optionally substituted, either in part or in whole, by compounds of the olefinic type, such as for example, acrylonitrile, alkyl acrylates, fumarates and maleates.

As previously mentioned herein, the association of catalytic complexes (III), (IV) and (V), (VI) with the substratum carrying the acid functional group (I) leads to the selective results observed in the linear addition reaction (1), in which the linkage to 3-butenoic acid (I) surprisingly occurs just almost entirely on end position "4".

Out of the starting products, 3-butenoic acid (I) is a compound industrially known as an intermediate, however, it may be prepared according to known or conventional techniques.

In their turn, radicals R; $R_1$; $R_2$; $R_3$, defined hereinbefore for 3-butenoic acid (I), may be also substituted by alkyl, alkoxyl, carboalkoxyl groups having from 1 to 4 carbon atoms, etc. and in general by groups which do not interfere with the reaction trend.

Among the catalysts based on Rhodium (III) and (IV), $RhCl1(PPh_3)_3$ (III) and $[Rh(COD)(PPh_3)_2]^+PF_6^-$ (IV) prove to be particularly effective: among the catalysts based on Nickel, Ni $[P(iPrO)_3]_4$ (V) and the mixture $Ni(COD)_2+4 P(iPrO)_3$ (VI), wherein the symbols have the meanings specified hereinbefore and iPr means isopropyl.

The reagents are employed in substantially stoichiometric molar ratios, while their concentration in the solvent is not critical for the purposes of the reaction.

Amounts of catalyst of the order of at least 0.001 millimoles per liter of reactive mass are already sufficient.

The reaction temperature is within the range of 60° C. to 140° C. approximately and it is selected in the aforesaid range depending on the other parameters, such as type of solvent, catalyst, concentrations, etc.

The reaction, as mentioned hereinbefore, is catalytic. For each mole of catalyst employed, a number of moles of product (IIa,b) variable as a function of the 3-butenoic substratum (I) and of the parameters is obtained, such number being in any case extraordinarily high.

For example, values of the order of 15,000 moles or more of linear acids $C_8$ per mole of Rhodium catalyst are easily attainable.

Also the reaction times vary as a function of the reaction general conditions: 2-3 hours may be sufficient for the completion of the reaction.

Octadienoic acids further substituted by successive reaction with butadiene in position "4" may be found among the products obtainable.

For example the acid:

$$CH_3CH=CHCH_2CH=CHCH_2COOH \qquad (IIa)$$

is capable of reacting with a butadiene molecule to give dodecatrienoic acid:

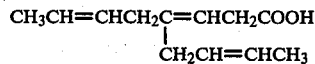

$$CH_3CH=CHCH_2\underset{\underset{CH_2CH=CHCH_3}{|}}{C}=CHCH_2COOH$$

and this acid, in its turn, by further reaction with a second molecule of butadiene, gives the acid:

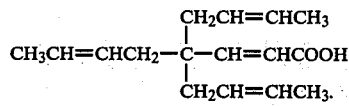

$$CH_3CH=CHCH_2-\underset{\underset{CH_2CH=CHCH_3}{|}}{\overset{\overset{CH_2CH=CHCH_3}{|}}{C}}-CH=CHCOOH$$

By suitably selecting the reaction conditions, these acids, which may be defined as octadienoic acids (IIa,b) substituted in position "4" by the 2-butenyl group, may be produced all together in the same reaction, after at least a portion of 3-butenoic acid (I) has been consumed. "Cis" and "trans" isomers and ramified by-products of the butenyl chain, as illustrated hereinabove, are present.

The products obtained are easily separated by means of conventional techniques, such as distillation of the solvent, neutralization of the acids, extraction, etc.

According to an effective embodiment, the process object of the present invention is conducted as follows.

The catalyst complex 3-butenoic acid (I), butadiene and the selected solvent, if any, are introduced into a closed reactor, in a nitrogen atmosphere and at atmospheric pressure. The resulting solution is maintained at the chosen temperature for the time required. The solvent is distilled off from the mixture, which is then treated with a dilute inorganic acid and extracted with ethyl ether, or also directly distilled under vacuum to obtain the final product.

The process, thanks to the simple and mild operating conditions, appears particularly advantageous. The economy of the synthesis starting from widely available products, such as butadiene and 3-butenoic acid, places the resulting products among the intermediates which are of interest in view of the uses previously mentioned.

SPECIFIC DESCRIPTION OF THE INVENTION

The invention will be described more in detail in the following examples, which are given for merely illustrative purposes.

Example 1 comprises also the hydrogenation of the octadienoic acid to octanoic acid.

In the examples, Ph=phenyl, COD=1,5-cyclooctadiene, iPr=isopropyl.

EXAMPLE 1

8.8 mg of $[Rh(COD)(PPh_3)_2]^+PF_6^-$ ($10^{-5}$ moles), 10.5 mg of $PPh_3$ ($4.0 \times 10^{-5}$ moles), (COD=1,5-cyclooctadiene, $PPh_3$=triphenylphosphine), 17.2 g of 3-butenoic acid (0.2 moles) and 13.5 g of butadiene (0.25 moles) were introduced, under a nitrogen atmosphere, into a pressure-resistant glass vessel.

The mixture was heated for 12 hours in an oil bath at 120° C.

At the end of the test, the unreacted 3-butenoic acid, partially isomerized to crotonic acid, was distilled at reduced pressure, and successively the reaction product, containing the octadienoic acids, linear and ramified in the ratio 87/13, 15.45 g, as a mixture of trans and cis isomers; only little amounts (1.2-1.4 g) of dodecatrienoic acids and isomers forming the tail products.

Thus, about 55% of the 3-butenoic acid put to reaction was converted into octadienoic acids, which coresponds to about 11,000 moles of acids per mole of complex.

By using 0.03 moles of 3-butenoic acid and 0.06 moles of butadiene, with the same amount of catalyst, a mixture was obtained in which, besides octadienoic acids, substantial amounts of dodecatrienoic acids and hexadecatetraenoic isomers were present.

EXAMPLE 2

0.111 g of Ni[(iPro)$_3$]$_4$, 1.0 g of 3-butenoic acid, 1.35 g of butadiene and 4 ml of acetonitrile were introduced, under a nitrogen atmosphere, into a pressure-resistant glass vessel. (iPr=isopropyl).

The whole was heated for 20 hours in a water bath maintained at 85° C. At the end of the test, the solvent was distilled, acidulated water was added and extraction was effected with ethyl ether; by evaporation of the solvent and distillation under vacuum there were obtained 1.60 g of a product, consisting of "3,6" and "2,6" octadienoic acids, linear and ramified in the ratio 80:20, 1.56 g, with minor amounts of dodecatrienoic acids and of ramified isomers.

The yield, calculated on 3-butenoic acid, was equal to 96%.

90 moles of 3-butenoic acid for each mole of complex were converted.

The compound obtained was hydrogenated to octanoic acid by means of catalytic hydrogenation at room temperature and pressure on palladium (10% on C.).

EXAMPLE 3

9.25 mg of RhCl1(PPh$_3$)$_3$, 5.16 g of 3-butenoic acid, 4.86 g of butadiene and 7.9 ml of acetonitrile were introduced, under a nitrogen atmosphere, into the glass vessel of example 1.

It was heated to 120° C. in an oil bath for 20 hours.

The solvent was distilled, whereupon, under reduced pressure, 3-butenoic acid, partially isomerized to crotonic acid, and the product were distilled too.

By operating according to example 1, it was possible to obtain 5.03 g of a product, consisting of octadienoic acids, linear and ramified in the ratio 85:15, 4.89 g, with minor amounts of dodecatrienoic acids and ramified isomers.

The yield, calculated on 3-butenoic acid, was equal to 58.2%.

3490 moles of 3-butenoic acid per mole of complex were con- verted into C-8. Most of the unreacted acid was recovered, in part as crotonic acid ($CH_3CH=CHCOOH$).

EXAMPLE 4

8.8 mg of $[Rh(COD)(PPh_3)_2]^+PF_6^-$ ($10^{-5}$ moles), 10.5 mg of $PPh_3$ ($4 \times 10^{-5}$ moles), 8 g of 3,6-octadienoic acids in a cis and trans mixture ($5.7 \times 10^{-2}$ moles) and 5.0 g of butadiene ($9.26 \times 10^{-2}$ moles) were introduced, under a nitrogen atmosphere, into the vessel of example 1.

The mixture was heated to 120° C. for 20 hours. By operating in like manner as described in example 1, about 3.75 g of a mixture of dodecatrienoic acids were obtained.

Thus, 1933 moles of octadienoic acids per mole of complex were converted into C-12 acids.

EXAMPLE 5

Under the same conditions of example 1,2-methyl-3-butenoic acid, butadiene and rhodium complex in the ratio of 120:240:1 were reacted.

After 20 hours at 120° C., a mixture of acids containing isomeric 2-methyloctadienoic acids was obtained.

EXAMPLE 6

Under the same conditions of example 3, 100 moles of 4-methyl-3-pentenoic acid and 200 mols of butadiene for each mole of rhodium complex were reacted, thus obtaining, after 20 hours at 120° C., 4,4-dimethyl-2,6-octadienoic acid as main product in the trans, trans form, besides little amounts of isomers.

The conversion was of about 50%.

What we claim is:

1. A process for preparing octadienoic acids, characterized in that butadiene is reacted with a 3-butenoic acid of formula (I):

$$RR_1C=CR_2CR_3HCOOH \quad (I)$$

wherein the symbols: R; $R_1$; $R_2$; $R_3$, either like or unlike one another, represent hydrogen atoms or alkyl groups, containing up to 4 carbon atoms, optionally containing double bonds, under an inert atmosphere, at a temperature of 60° C. to 140° C., in substantially equimolar ratios and in the presence of at least 0.001 millimoles per liter of reacting mass of at least a catalyst selected from the phosphinic complexes of Rhodium (III, IV), the phosphitic complexes of Nickel (V) and the mixture (VI) having the formulae:

$$Rh[P(R_4)_3]_nL_mX \quad (III)$$

$$Rh[P(R_4)_3]_nL^+_pY^- \quad (IV)$$

$$Ni[P(OR_5)_3]_4 \quad (V)$$

$$Ni(COD)_2+qP(OR_5)_3 \quad (VI)$$

wherein $R_4$ is a hydrocarbyl group having up to 15 carbon atoms, L is a linear or cyclic olefin having from 2 to 10 carbon atoms or a chelating olefin having from 6 to 10 carbon atoms; n is an integer from 1 to 3, m is an integer from 0 to 2, such that $n+m=2$ or 3, p is an integer from 0 to 3, such that $n+p=3$ or 4; COD represents 1,5 cyclooctadiene and q is an integer from 1 to 4; X is an anion selected from the group consisting of haloid anions, and the anions of carboxylic acids having up to 4 carbon atoms; Y is a low coordinating anion selected from the group consisting of $BF_4^-$, $PF_6^-$, $ClO_4^-$, $B(C_6H_5)_4^-$; $R_5$ is an aryl or an alkyl having up to 12 carbon atoms.

2. The process according to claim 1, in which the olefin L, contained in the catalyst of formula (III) or (IV), is selected from the group consisting of ethylene, cyclooctene, norbornene, 1,5-cyclooctadiene, 1,5-hexadiene, norbornadiene and dicyclopentadiene.

3. The process according to claim 22 in which ($R_5$) in the catalyst of formula (V) or (VI), is selected from the group consisting of aryl and alkyl groups having up to 12 carbon atoms.

4. The process according to claim 1, characterized in that it is conducted in the presence of an excess of free phosphinic or phosphitic compound $P(R_4)_3$ or $P(OR_5)_3$, as defined in claim 1.

5. The process according to claim 1, characterized in that the catalyst is selected from the group consisting of $RhCl(PPh_3)_3$; $[Rh(COD)(PPh_3)_2]^+PF_6^-$; $Ni[P(i-PrO)_3]_4$; and the mixture $Ni(COD)_2+4P(iPrO)_3$; in which iPr means isopropyl; Ph means phenyl and COD means 1,5-cyclooctadiene.

6. The process of claim 1, in which there is used a catalyst complex (III) in which X is the hydrochloric anion.

7. The process according to claim 1, characterized in that it is conducted in an organic medium consisting of a compound not containing aliphatic unsaturations, selected from the group consisting of alcohols, ethers, esters, hydrocarbons, nitriles and carboxylic acids.

8. The process according to claim 1, in which $R_4$ in the catalyst of formula (III) or (IV), is selected from the group consisting of aliphatic and aromatic groups having up to 15 carbon atoms.

9. The process according to claim 8, in which $R_4$ is selected from the group consisting of propyl, isopropyl, butyl, cyclohexyl, phenyl, tolyl, anisyl, diphenyl and naphthyl.

10. The process according to claim 3, in which ($R_5$) is selected from the group consisting of isopropyl and phenyl.

11. The process according to claim 8 in which the 1,5-cyclooctadiene in the catalyst of formula (VI), is at least partially substituted by an olefinic compound.

12. The process according to claim 1, characterized in that 3-butenoic acid of formula (I) contains substituent groups which are inert under the reaction conditions, and selected from the group consisting of alkyl, alkoxyl and carboalkoxyl groups having up to 4 carbon atoms.

13. The process of claim 23, in which the compound not containing aliphatic unsaturations has a boiling point below that of the 3-butenoic acid.

14. The process according to claim 11, in which the olefinic compound substituent in the 1,5-cyclooctadiene is selected from the group consisting of acrylonitrile, alkyl acrylates, fumarates and maleates.

15. The process according to claim 7, characterized in that the organic medium is selected from the group consisting of ethyl alcohol, anisole, ethyl acetate, benzene, acetonitrile and acetic acid.

* * * * *